(12) United States Patent
Phillips et al.

(10) Patent No.: US 12,419,505 B2
(45) Date of Patent: Sep. 23, 2025

(54) STEERABLE ENDOSCOPE SYSTEM AND METHOD

(71) Applicant: Covidien LP, Mansfield, MA (US)

(72) Inventors: Matthew J. Phillips, Carlsbad, CA (US); Amand Kasimatis, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 193 days.

(21) Appl. No.: 17/557,505

(22) Filed: Dec. 21, 2021

(65) Prior Publication Data

US 2022/0225859 A1 Jul. 21, 2022

Related U.S. Application Data

(60) Provisional application No. 63/139,591, filed on Jan. 20, 2021.

(51) Int. Cl.
*A61B 1/005* (2006.01)
*A61B 1/05* (2006.01)

(52) U.S. Cl.
CPC ............ *A61B 1/0057* (2013.01); *A61B 1/05* (2013.01)

(58) Field of Classification Search
CPC ............ A61B 1/00064; A61B 1/00066; A61B 1/00071; A61B 1/00078; A61B 1/00098; A61B 1/0005–00052; A61B 1/00057; A61B 1/008; A61B 1/009; A61B 1/012; A61B 1/00004–00006; A61B 2017/003; A61B 2017/00318; A61B 2017/00323; A61B 2017/00327

USPC .................................................. 600/136–152
See application file for complete search history.

(56) References Cited

U.S. PATENT DOCUMENTS

| | | | | |
|---|---|---|---|---|
| 5,372,587 A | * | 12/1994 | Hammerslag | A61M 25/0144 604/95.04 |
| 2003/0233027 A1 | * | 12/2003 | Ewers | A61B 1/00082 600/114 |
| 2007/0135803 A1 | * | 6/2007 | Belson | A61B 1/00154 606/1 |
| 2016/0331213 A1 | * | 11/2016 | Kim | A61B 1/00048 |
| 2017/0165456 A1 | | 6/2017 | Tutungi et al. | |
| 2020/0254204 A1 | | 8/2020 | Moffat et al. | |
| 2021/0045626 A1 | * | 2/2021 | Hsu | A61B 1/307 |

FOREIGN PATENT DOCUMENTS

| | | |
|---|---|---|
| CN | 107 744 405 A | 3/2018 |
| EP | 1857039 A2 | 11/2007 |
| EP | 3 517 017 A1 | 7/2019 |
| JP | 4-414827 B2 | 2/2010 |
| WO | 2022/133248 A1 | 6/2022 |
| WO | 2022/266500 A1 | 12/2022 |

OTHER PUBLICATIONS

International Search Report and Written Opinion for International No. PCT/US2022/011931 mailed Apr. 7, 2022 (13 pages).

\* cited by examiner

*Primary Examiner* — Ryan N Henderson
*Assistant Examiner* — Pamela F Wu (57) ABSTRACT

A steerable endoscope is provided that includes a tubular body with a plurality of wires that, when deflected in a non-axial direction, cause a distal end of the endoscope to change orientation. A controller for the endoscope generates instructions to cause the deflection of one or more of the plurality of wires according to a steering input.

20 Claims, 11 Drawing Sheets

STEERABLE ENDOSCOPE SYSTEM AND METHOD

CROSS-REFERENCE TO RELATED APPLICATION PAPERS

This application claims benefit of U.S. Patent Application No. 63/139,591, filed 20 Jan. 2021 and which application is incorporated herein by reference. To the extent appropriate, a claim of priority is made to the above-disclosed application.

BACKGROUND

The present disclosure relates generally to medical devices and, more particularly, to steerable endoscopes with deflection-based steering, and related methods and systems.

Medical endoscopes are long, flexible instruments that can be introduced into a cavity of a patient during a medical procedure in a variety of situations to facilitate visualization and/or medical procedures within the cavity. For example, one type of scope is an endoscope with a camera at its distal end. The endoscope can be inserted into a patient's mouth, throat, or other cavity to help visualize anatomical structures, or to facilitate procedures such as biopsies or ablations. The endoscope may include a steerable distal tip that can be actively controlled to bend or turn the distal tip in a desired direction, to obtain a desired view or to navigate through anatomy. However, these steerable scopes can be difficult to maneuver into the desired location and orientation within a patient's anatomy.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In an embodiment, a steerable endoscope system includes an endoscope and a controller. The endoscope has a tubular body and a plurality of wires disposed within the tubular body. Each wire of the plurality of wires is coupled to an endoscope distal end such that, upon deflection of one or more wires of the plurality of wires in a non-axial direction, the endoscope distal end changes orientation. The controller is in communication with the endoscope and has a display screen responsive to a user command to steer the endoscope; and a processor that receives the user command and generates instructions to change the orientation of the endoscope distal end. The system also includes at least one clamp, wherein the instructions activate the at least one clamp to clamp the one or more wires, wherein the one or more wires, when clamped, are deflected in the non-axial direction to conform to a contoured surface of the at least one clamp to cause the change the orientation of the endoscope distal end.

In an embodiment, an endoscope system includes an endoscope and a controller. The endoscope has a tubular body and a plurality of wires. Each wire of the plurality of wires is coupled to an endoscope distal end and an endoscope proximal end, wherein the endoscope distal end is at a first orientation when the plurality of wires are not deflected. The controller is in communication with the endoscope and receives a user steering input and generates instructions to cause coordinated deflection of the plurality of wires in a non-axial direction to transition the endoscope distal end from the first orientation to a second orientation according to the user steering input.

In an embodiment, a method for steering of an endoscope is provided that includes the steps of receiving, via a touch screen display, a user input to change an orientation of an endoscope distal end; and in response to the user input, activate a wire deflector to apply a non-axial deflection force to deflect one or more wires of a plurality of wires disposed within an endoscope, wherein the non-axial deflection force applied to the one or more wires is transferred to the endoscope distal end to change the orientation of the endoscope distal end, and wherein the non-axial deflection force is in a direction that is outside of a plane extending through the one or more wires.

In an embodiment, an endoscope includes a tubular body comprising a proximal end and a distal end a plurality of wires within a central passage of the tubular body and extending from the distal end and the proximal end, and one or more wire deflectors that, when activated, apply a non-axial force to at least one wire of the plurality of wires to deflect the at least wire and cause a change in orientation of the distal end.

Features in one aspect or embodiment may be applied as features in any other aspect or embodiment, in any appropriate combination. For example, any one of system, laryngoscope, handle, controller, endoscope, or method features may be applied as any one or more other of system, laryngoscope, controller, endoscope, or method features.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

A medical scope or endoscope as provided herein is a thin, elongated, flexible instrument that can be inserted into a body cavity for exploration, imaging, biopsy, or other clinical treatments, including catheters, narrow tubular instruments, or other types of scopes or probes. Endoscopes may be navigated into the body cavity (such as a patient's airway, gastrointestinal tract, oral or nasal cavity, or other cavities or openings) and be steered into by the user via advancement of the distal end to a desired position and, in certain embodiments, biomimetic motion of the endoscope. Endoscopes may be tubular in shape.

Advancement of long, flexible medical devices into patient cavities is typically via force transferred from a proximal portion of the device (outside of the patient cavity), that results in advancement of the distal tip within the patient cavity. For example, a doctor or other caregiver holding a proximal portion (such as a handle) of the medical device outside of the patient cavity pushes downward or forward, and the resulting motion is transferred to the distal tip, causing the tip to move forward within the cavity. Similarly, a pulling force applied by the caregiver at the proximal portion may result in retreat of the distal tip or movement in an opposing direction out of the patient cavity. However, because patient cavities are not regularly shaped or sized, the endoscope moves through a tortuous path, and the transferred force in a pushing or pulling motion from the proximal end may not result in predictable motion at the distal tip.

Provided herein is a steerable endoscope with controlled steering in three dimensions that facilitates fine steering within curving paths of a patient passageway. The endoscope includes wires that extend along a length of the endoscope and translate steering inputs into desired movement at the endoscope distal tip via deflection of one or more of the wires in a non-axial direction, e.g., in a direction non-axial to the length axis of the steerable endoscope. Applying force an axial direction along the length axis of an endoscope, as in a conventional arrangement, requires more applied force, and power, than deflection-based steering that applies force a non-axial direction to steer the endoscope distal tip in three dimensions. Thus, a lower total force can power the disclosed deflection-based steering relative to conventional axial force application. The steering inputs and control can be provided via a coupled controller that is located outside of the patient and that receives steering inputs from an operator. In some embodiments, the steering inputs cause the controller to activate mechanical or pneumatic elements, magnetic elements, and/or electromagnetic elements that deflect one or more wires of the steerable endoscope in a direction and by a distance consistent with the desired steering outcome.

Figure 1:
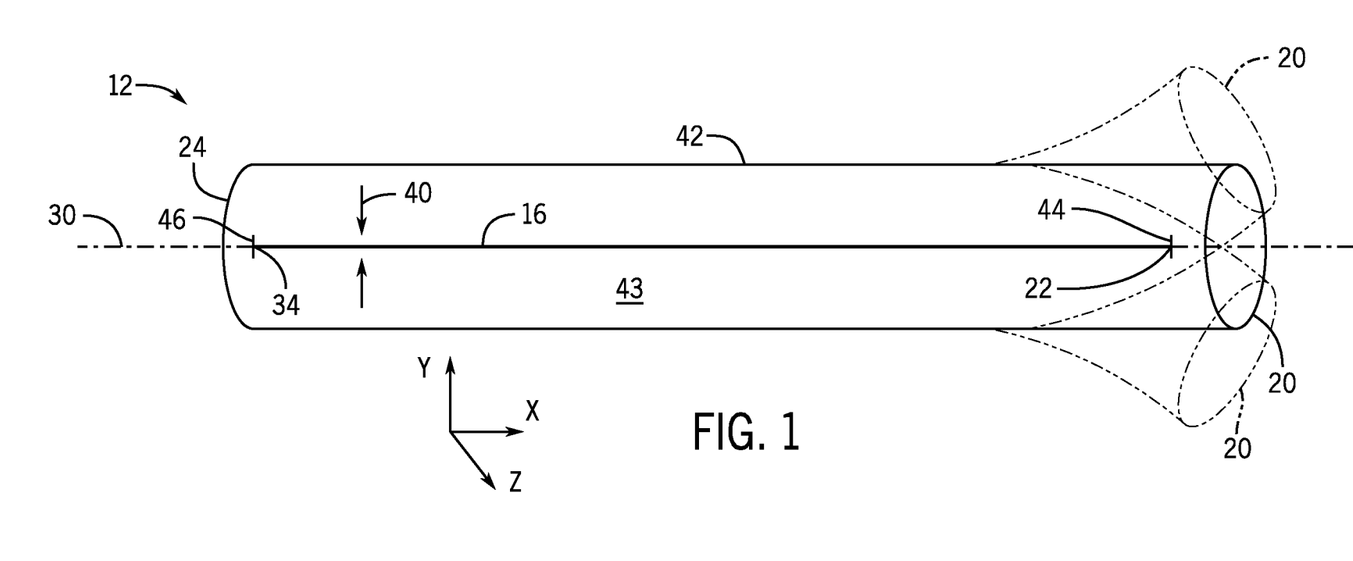
FIG. 1 is a schematic illustration of a steerable endoscope, according to embodiments of the present disclosure.

FIG. 1 is a schematic illustration of wire-based deflection to steer an endoscope 12. The endoscope 12, e.g., a steerable endoscope, includes one or more wires 16 (e.g., two, three, four, or more) that run along a length of the endoscope 12 in a proximal-distal direction and that are deflected to steer the endoscope 12. While the illustrated embodiment shows a single wire 16, it should be understood that coordinated deflection forces applied to multiple wires 16 of the endoscope 12 results in 360 degree steering capabilities of the endoscope distal end 20. The wires 16 of the steerable endoscope are fixed to a distal coupling point 22 at or near the endoscope distal end such that internal deflection at a more proximal position, e.g., near the endoscope proximal end 24, causes corresponding movement of the endoscope distal end 20. In an embodiment, the wire 16 runs along an axis 30 extending through the endoscope proximal end 24 and distal end 20.

Deflection of the wire 16 at a proximal location by an applied deflecting force, illustrated by example deflecting force arrows 40 is translated to the wire distal end 22 to change an orientation of the endoscope distal end 20. The wire 16 can be deflected in any non-axial direction (e.g., not along the axis 30 or out of plane from a plane that includes that wire 16) in the x, y, or z direction such that the direction of deflecting force is transverse or non-axial to the wire 16 and according to the desired steering. A non-axial applied force is the most efficient to result in axial displacement of the wire 16. The amount of applied force may depend on the angle of non-axial force relative to the wire 16. In an embodiment, an orthogonal (e.g., perpendicular) force may be more efficient than force directions that are non-axial and also non-orthogonal. The resultant change in orientation of the distal end 20 is related to the direction of the applied force 40, the amount of applied force 40, and the position of the wire 16 relative to the tubular body 42, e.g., the circumferential position of the distal coupling point 22. In the illustrated embodiment, an applied orthogonal (e.g., perpendicular relative to the axis of the wire 16) force 40 causes movement (shown in dashed lines of the distal end 20) of the distal end 20 in an opposite direction to the force arrow 40. In multi-wire embodiments, the orientation change is a function of the combined deflections of each deflected wire 16. Further, the orientation change may be a result of simultaneous deflection forces or sequential application of deflection forces applied to each deflected wire 16. Accordingly, the wire deflectors disclosed herein may be activated sequentially to cause incremental orientation changes applied within a particular time window (e.g., 1-30 seconds) that, in total, result in the desired orientation change.

The applied non-axial force may be, as illustrated, (perpendicular) to the wire 16 or may be applied at a nonorthogonal angle (e.g., at an angle of 5-85 degrees) relative to the wire 16. In an embodiment, the non-axial force is not aligned with the axis 30 of the wire 16. That is, in an embodiment, the non-axial force is not a push/pull force in a direction along the axis 30 and/or is not parallel to the axis 30. Further, the non-axial force may be applied from one or more directions relative to the wire 16 (e.g., emanating from different possible 360 degree locations). While the wire or wires 16 may be generally axial between the endoscope proximal end 24 and endoscope distal end 20, portions of the wire or wires 16 may also curve, bend, or extend at an angle within the endoscope 12. Thus, as provided herein, the non-axial or non-axial force may be non-axial or non-axial relative to a portion of wire 16 corresponding to the location of deflecting force application and/or non-axial or non-axial relative to the axis 30 running through endoscope proximal end 24 and distal end 20.

Force application in a non-axial direction to deflect the wire 16 provides a mechanical advantage over applied axial forces, i.e., pulling or pushing on the wire 16. A lower applied non-axial force can achieve a desired orientation change of the distal end 20 relative to a required force in a pulling or pushing-type arrangement. Thus, overall power levels are reduced to steer the endoscope.

The wire or wires 16 run within or along a tubular body 42 of the endoscope 12. Each wire 16 may run through a dedicated internal lumen or may be routed through a central bore 43 of the endoscope 12. The body 42 is at least partially flexible to the endoscope distal end 20 to change orientation in response to wire deflection. In an embodiment, the endoscope proximal end 24 is coupled to a controller in operation and, thus, only the distal end 20 is free to move or change orientation in response to wire deflection. Each wire 16 of the endoscope can be pulled taut (with little to no slack) with preset tension or load when not deflected between the wire distal end 22 and a proximal end 34. At least the wire distal end 22 is fixed (adhered to, bonded to, tied to, coupled to, clamped, integrally coupled to, etc.) relative to the endoscope distal end 20 such that the deflecting force transfers to the endoscope distal end 20. In an embodiment, the wire 16 has substantially no slack and no load or with zero tension between the wire distal end 22 and the proximal end 34 when in an undeflected configuration. When deflected, tension in the wire 16 is increased. The wire 16 may be a relatively inelastic but conformable or flexible material (metal, memory metal, polymer), and removal of the deflecting force causes the wire or wires 16 to return to the undeflected configuration or a neutral configuration. In an embodiment, the undeflected configuration is a generally axial configuration while the deflected configuration causes the wire 16 to deviate from the generally axial configuration by bending or curving at one or more locations according to the applied non-axial force.

The wire distal end 22 may be coupled to a distal support structure 44, such as a resilient ring, bridge, or strut that holds the wire distal end 22 distally in place and facilitates transfer of the deflecting force of the wire 16 to the endoscope distal end 20. As provided herein, each wire 16 may be coupled to a dedicated distal support structure 44 or may share the distal support structure 44 with another wire or wires 16. Each wire 16 may additionally or alternatively be coupled to one or more proximal support structures 46. The wire proximal end 34 may be within the endoscope 12 or may extend beyond the endoscope proximal end 24 to couple to a controller.

Figure 2:
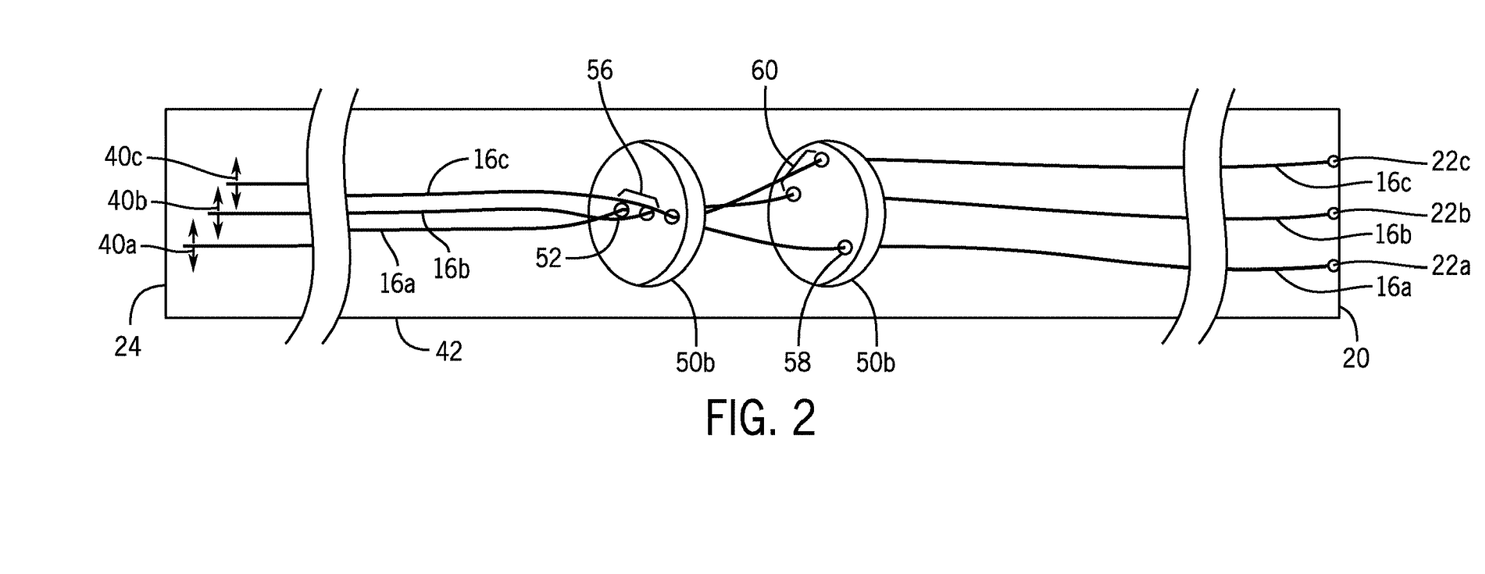
FIG. 2 is a schematic illustration of a steerable endoscope having a multi-wire arrangement, according to embodiments of the present disclosure.

The endoscope distal end 20 can be steered in 360 degrees based on controlled non-axial deflection forces applied to a selected wire or wires 16, independently or in combination. FIG. 2 shows an example three wire arrangement in which the wires 16a, 16b, 16c extend along the endoscope 12, and the respective wire distal ends 22a, 22b, 22c are circumferentially distributed about the endoscope distal end 20 (e.g., spaced approximately 120 degrees apart from one another). Other arrangements including more or fewer wires 16 and/or with different spacing are also contemplated. Depending on the desired orientation change, deflecting forces 40a, 40b, 40c applied at a more proximal location are translated down the length of the endoscope 12. A deflecting force 40 applied to the wire or wires 16 causes a desired orientation change of the endoscope distal end 20 through force translated to a particular location or region of the endoscope distal end 20 corresponding to the wire distal end 22.

While the wire distal ends 22a, 22b, 22c are spaced apart about the circumference of the endoscope distal end 20 to facilitate the endoscope steering, it may be beneficial to guide the wires 16 in a side-by-side or planar arrangement at more proximal locations in the endoscope via a structural support, such as spacer 50 that includes passages 52 or grooves that correspond to the desired spacing 56 between the wires 16. In one example, the side-by-side arrangement permits the wires 16 to align with deflecting structures or surfaces of the endoscope 12 or a coupled controller. Further, the planar arrangement may conserve interior space of the endoscope or may permit less complex manufacturing by permitting portions of the wires 16 to run through the central passage 43 of the endoscope 12 rather than through separate dedicated lumens running through an outer wall of the endoscope 12. In an embodiment, the spacer 50 is shaped to accommodate any other channels or lumens of the endoscope 12 and can maintain a relatively narrow spacing of the wires 16 in cases where working channels are also present. An arrangement in which the wires 16 are in a side-by-side arrangement also allows for single direction actuation (on multiple wires) to be transformed into 360 degree motion via selective deflection of one wire 16, a subset of the wires 16, or all of the wires 16 simultaneously. Depending on the selective activation, e.g., which wire 16 or wires 16 are deflected, different orientation changes are possible, with the range of possibilities facilitating 360 degree steering.

In another example, the spacer 50 is positioned past a midpoint of the endoscope 12, e.g., closer to the endoscope distal end 20, to reduce curvature bias during steering. In operation, the endoscope 12, when inserted in the patient, follows a curve of the patient airway such that the endoscope has an interior curve and an exterior curve. Wires 16 that are positioned closer to the interior curve of the endoscope 12 would be more curved than those that follow the exterior curve. The different levels of curvature between individual wires 16 in such a case would lead to different responsiveness to applied deflection forces. In an embodiment, the use of the spacer 50a to space the wires 16 closer together along at least a portion of a length of the endoscope 12 (e.g., at least 50% or at least 75% of a proximal-distal length dimension) reduces the effects of curvature bias between the wires 16 by reducing differences in curvature between the wires 16. Multiple spacers 50 may be used to hold the wires 16 in a desired side-by-side arrangement in more proximal regions of the endoscope 12.

The wires 16 can extend distally away from the spacer 50a and at an angle corresponding to the desired spacing at the wire distal ends 22. Additional spacers 50 can be incorporated to maintain or change the spacing of the wires 16 within the endoscope 12. The endoscope 12 can include a spacer 50b with passages 58 having spacing 60 that generally aligns with the larger spacing at the wire distal ends 22. Thus, a first spacer 50a includes passages 52 having a smaller spacing relative to passages 50 of a second spacer 50b located distally of the first spacer 50b.

An individual wire 16 can be deflected by mechanical, pneumatic, magnetic, and/or electromagnetic deflection arrangements that apply non-axial force in a non-axial direction to deflect the wire 16. FIG. 3-7 illustrate examples of wire deflection arrangements that may be incorporated into or coupled to the endoscope 12 to deflect one or more of the wires 16 and, as a result, change an orientation of the endoscope distal end 20. Each individual wire 16 may be coupled to a dedicated wire deflector, or a wire deflector may operate simultaneously on multiple wires 16. The depicted wire deflector arrangements may be used in combination with one another in the endoscope 12. Further, it should be understood that the depicted wire deflection arrangements may be incorporated into the endoscope 12 at proximal, intermediate, and/or distal positions. In certain embodiments, activation of the wire deflectors provided herein may be controlled by a coupled device, such as a controller (see FIG. 8). The wire deflectors as provided herein are capable of reversibly deflecting the wire 16 such that the wire 16 can return to an undeflected state or configuration when the wire deflector is inactive or is moved away from (e.g., out of direct contact with) or retracted from the wire 16. Activation of the wire deflector or movement of the wire deflector to contact the wire 16 bends the wire 16 within the endoscope 12, causing an area of local tension, that in turn is transferred to the endoscope distal end 20.

Figure 3A:
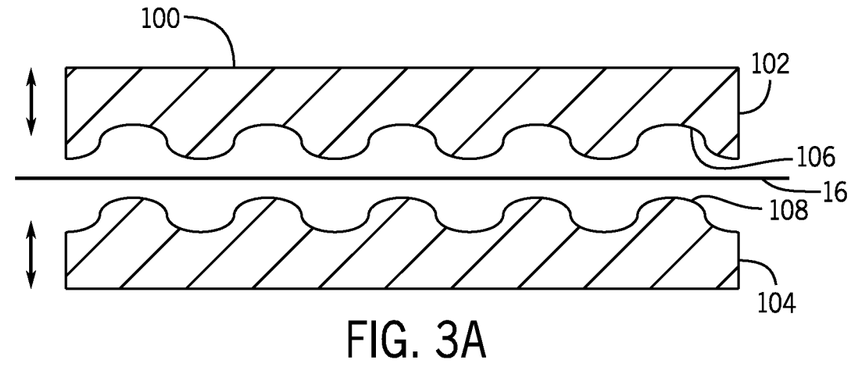
FIG. 3A is a schematic illustration of a clamp-type wire deflector with the wire in an undeflected configuration, according to embodiments of the present disclosure.
Figure 3B:
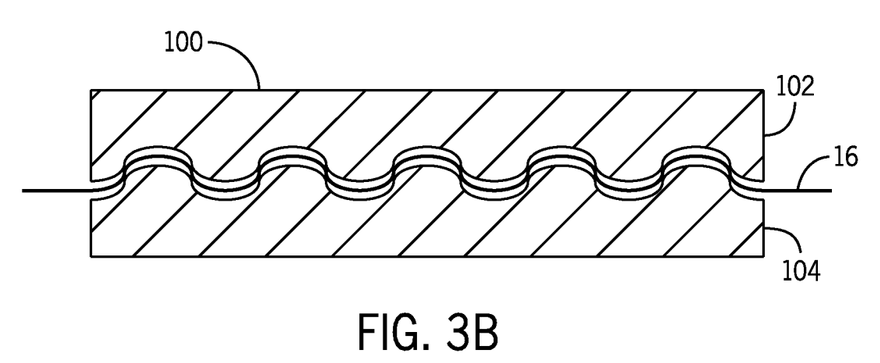
FIG. 3B is a schematic illustration of the clamp-type wire deflector of FIG. 3A with the wire in a deflected configuration, according to embodiments of the present disclosure.

FIGS. 3A-3B show an example of a wire deflector clamp 100. The wire 16 passes through a top section 102 and a bottom section 104 of the clamp 100. When the top section 102 and the bottom section 104 are not in contact with one another and with the wire 16, the wire 16 is undeflected as shown in FIG. 3A. When the top section 102 and the bottom section clamp the wire 16, as shown in FIG. 3B, the wire 16 conforms to the respective contoured surfaces 106, 108 of the clamp 100. This effectively shortens the axial length of the wire 16 by displacing wire length along the various contours of the contoured surfaces 106, 108 of the clamp 100. Thus, the total length displacement, and associated axial decrease in length of the wire 16 along a proximal-distal axis, is related to a surface area of the contoured surfaces 106, 108. Increased surface area causes more length displacement of the wire 16 and axial shortening, which in turn results in a greater change in orientation of the endoscope distal end 20. Thus, in an embodiment, the endoscope 12 can include different clamps 100 along the length of the wire 16 and/or distributed about a circumference of the wire 16, each with different length displacement capabilities depending on the arrangement and surface area encompassed by the contours of the associated contoured surface.

A controller can activate one or more selected clamps 100 from the available clamps 100, depending on the steering input and the desired magnitude of the orientation change of the distal end 20. For example, individual clamps 100 may be activated to cause incremental orientation changes applied sequentially, e.g., to cause an inchworm-like motion of the endoscope distal end 20. These incremental changes are controlled to result in a desired total orientation change of the distal end 20. The contoured surface or surfaces (e.g., contoured surfaces 106,108) of the clamp 100 can include peaks and valleys or sinusoidal curves. The contoured surface may include regular or irregular contours.

When the clamp 100 is activated or closed around the wire 16, the wire 16 is deflected. The clamping motion of one or both of the clamp sections 102, 104 is generally orthogonal/perpendicular to the axis of the wire 16. However, the contoured surfaces 106, 108 act to apply deflecting forces to the wire 16 at various angles and distances based on their shapes.

In an embodiment, the top section 102 or the bottom section 104 are stationary, and only one clamp section moves relative to the wire 16. The other, stationary, an interior contoured surface of the clamp 100 (e.g., the bottom surface 104) may be formed in an interior wall, lumen, or surface of the tubular body 42 (FIG. 1). The wire 16 is positioned within the endoscope to align with the interior surface. In one embodiment, the wire 16 is proximate to an interior contoured surface that extends along at least a portion of the length of the endoscope 16. One or more movable clamp sections (e.g., the top section 102) can be activated to move toward the interior contoured surface. The clamp 100 may be a clamp array with multiple movable clamp sections that clamp the wire 16 against the interior contoured surface.

A low compression force applied by orthogonal motion of the clamp 100 yields a relatively high tension in the wire 16 compared to a similar force applied instead in an axial direction, thus providing a mechanical force advantage for endoscope steering. That is, less force applied in a non-axial is required to achieve a desired orientation change of the endoscope distal end 20. The tension in the wire 16 is related to the length displacement, and the contoured surfaces 102, 104 may be shaped to displace a particular length when mated or clamped together. In one embodiment, one section (e.g., the top section 102) of the clamp 100 is movable, and the contoured surface of the mating section (e.g., the bottom section 104) is stationary and is formed in a wall or surface of the tubular body or incorporated into the spacer 50. In an embodiment, the top section 102 and/or the bottom section 104 of the clamp 100 may rotate into and out of the clamped position to avoid reduce friction of movement.

Other mechanical wire deflectors are also contemplated. In an embodiment, the shortening of the wire 16 may be achieved by activating a pin, paddle, or other structure to directly apply non-axial force to the wire 16. The contact surface of such a structure may be contoured or shaped to promote bending of the wire 16 around the contact surface during deflection. Retraction of the structure causes the wire 16 to return to the undeflected configuration.

Figure 4:
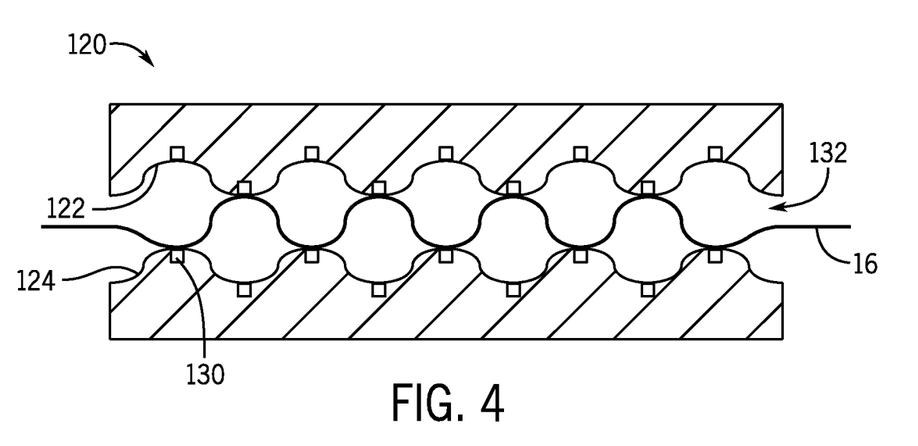
FIG. 4 is a schematic illustration of an activated surface wire deflector, according to embodiments of the present disclosure.

FIG. 4 is an example of a magnet-based wire deflector 120 that deflects the wire 16 using at least one activated contoured surface, illustrated as a top contoured surface 122 and a bottom contoured surface 124. Magnetic, electromagnetic, or electrostatic wire deflection may be used for low power steering, e.g., relatively lower power relative to mechanical movement. Rather than moving the surfaces 122,124 to clamp the wire 16, individual addressable magnets 130 on or in the surfaces 122, 124 are selectively activated to attract the wire 16 (e.g., a steel wire) to displace a wire length associated with a desired steering outcome. In the illustrated example, the deflection can be towards portions of the top contoured surface 122 as well as portions of the bottom contoured surface 124 depending on the set of activated magnets 130. Activation of different sets of magnets 130 creates different displacement lengths of the wire 16 and, thus, introduces the potential for tuning different deflection forces to achieve a desired steering at a more granular level and with improved resolution relative to those associated with axial pulling or pushing. The number and position of magnets 130 relative to each wire 16 can be set to a desired steering resolution, and user steering inputs are translated to a magnet activation pattern associated with a particular orientation change of the user steering input.

The wire 16 is positioned within a space 132 that is sized and shaped to permit wire deflection. In an embodiment, the magnet-based wire deflector 120 is integrated into a lumen of the endoscope or into a spacer (e.g., spacer 50, FIG. 2) or other structural component (e.g., bridge or strut) through which the wire or wires 16 pass.

Figure 5:
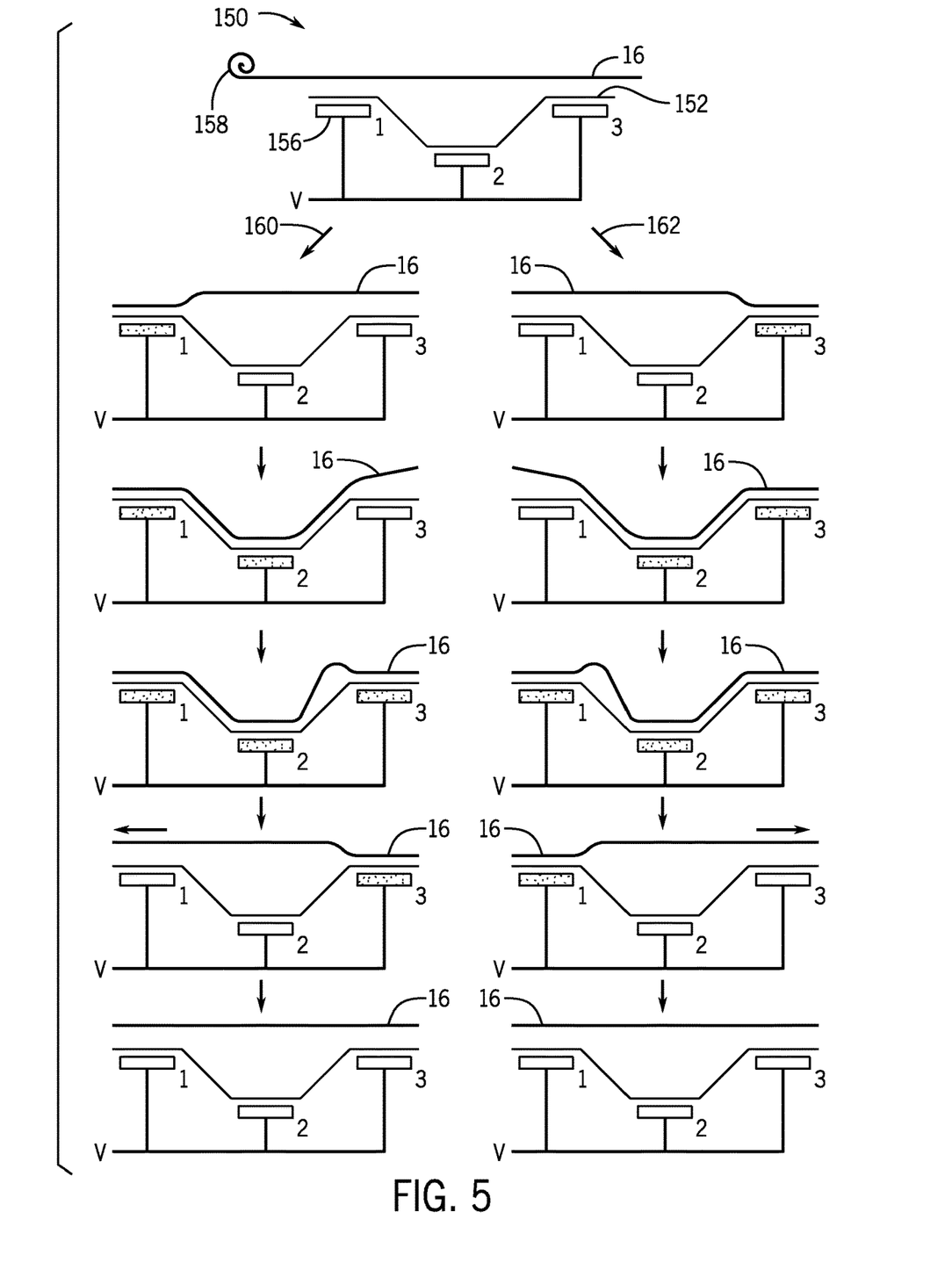
FIG. 5 is a schematic illustration of an activated surface wire deflector that activates to cause proximal or distal wire displacement, according to embodiments of the present disclosure.

FIG. 5 is an example showing a wire deflector 150 with a one-sided activated surface 152 that deflects the wire 16 and, additionally or alternatively, applies axial force to the wire 16. The one-sided activated surface 152 may be incorporated into an interior surface or lumen of the tubular body 42. Magnets 156, labeled by way of example as 1, 2, and 3, on or in the activated surface 152 can be selectively activated in a particular combination and order to deflect the wire 16. While the illustrated arrangement includes three magnets, other combinations are also contemplated that include one, two, four, or more magnets that act on one or more wires 16. In an embodiment, activation of the magnets in a particular order and combination causes localized wire tension or slack. A spool 158, located proximally and/or distally of the magnets 156, can rotate to release more wire 16 or wind up any temporary slack as a result of the magnet deflection. Thus, in an embodiment, the length displacement caused by non-axial force of the magnets may be used to move the wire 16 in a proximal or distal direction to steer the endoscope 12.

A workflow 160 shows a magnet activation pattern in a three-magnet arrangement that results in displacement of the wire 16 in a proximal direction. First, magnet 1 is activated to provide an anchor point so that wire movement is limited to a single direction during the subsequent step. Next, magnets 1 and 2 are simultaneously active (e.g., activation of magnet 2 is added to the already-active magnet 1) to attract and pull down the wire 16 to the right and while magnet 3 is not activated. This results in a bending of the wire 16 and an area of local slack near magnet 3. Magnet 3 is then activated while maintaining activation of magnets 1 and 2 to hold the local slack in place relative to the activated surface 152. Finally, magnets 1 and 2 are released while magnet 3 is still active, becoming the new anchor point, which pushes the local slack in the wire 16 in a proximal direction as the wire straightens and slides to the left. Another workflow 162 shows the activation pattern of magnets to displace the wire 16 in a distal direction. First, magnet 3 is activated to provide an anchor point so that wire movement is limited to a single direction during the subsequent step. Next, magnets 2 and 3 are simultaneously active (e.g., activation of magnet 2 is added to the already-active magnet 3) to attract and pull down the wire 16 and while magnet 1 is not activated. This results in a bending of the wire 16 and an area of local slack near magnet 1. Magnet 1 is then activated while maintaining activation of magnets 2 and 3 to hold the local slack in place relative to the activated surface 152. Finally, magnets 2 and 3 are released while magnet 1 is still active, becoming the new anchor point, which pushes the local slack in the wire 16 in a distal direction as the wire straightens and slides to the right. During the workflows 160, 162, to anchor movement in a desired direction, at least magnet 1 or magnet 3, or both, are active until the completion of the incremental wire movement to provide an anchor point. At the completion of each workflow 160, 162, the wire can return to neutral while all magnets are inactive.

The workflows 160, 162 can be combined and performed in series a desired number of times to translate the wire 16 in proximal and distal directions using non-axial deflection forces generated by magnet activation. Each iteration of the workflow 160, 162 causes an incremental movement on the proximal or distal direction. Multiple iterations of the workflow 160 causes proximal movement of the wire 16, and multiple iterations of the workflow 162 causes distal movement of the wire 16. The repetition of the workflow 160 and/or the workflow 162 can be controlled based on user input indicative of a desired steering change.

In addition selective activation of clamp 100s (FIGS. 3A-B) can create loose proximal regions of wire 16 that can be sequentially coiled (e.g., into spool 158), pinched, and released in a manner similar to the sequential magnet activation of FIG. 5. That is, individual clamps 100 can be activated in different patterns to translate the wire 16 in proximal and distal directions using transverse deflection forces generated by clamp activation. Accordingly, one or more of the magnets 1, 2, 3 can be replaced with selectively activated clamps 100 to achieve a similar effect.

Figure 6A:
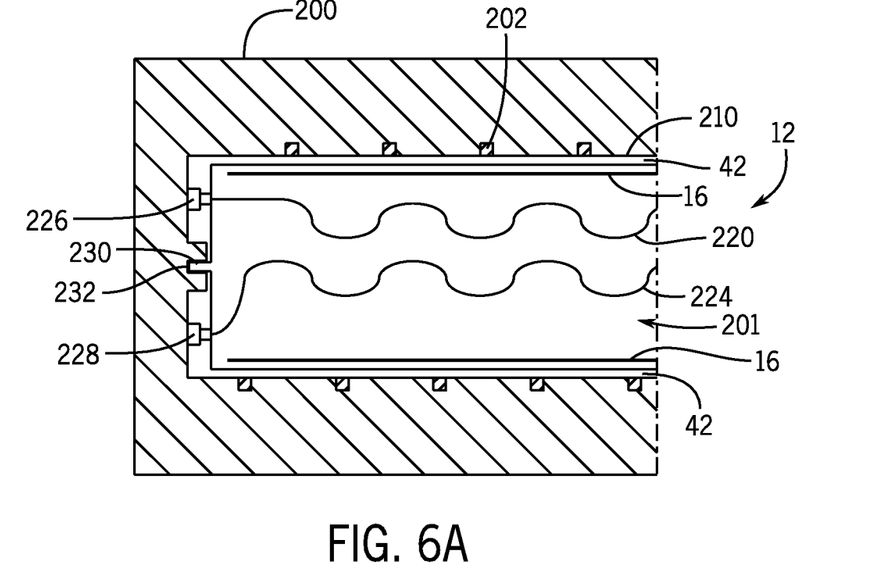
FIG. 6A is a schematic illustration of a connector of a controller device that includes a magnet-based wire deflector, according to embodiments of the present disclosure.
Figure 6B:
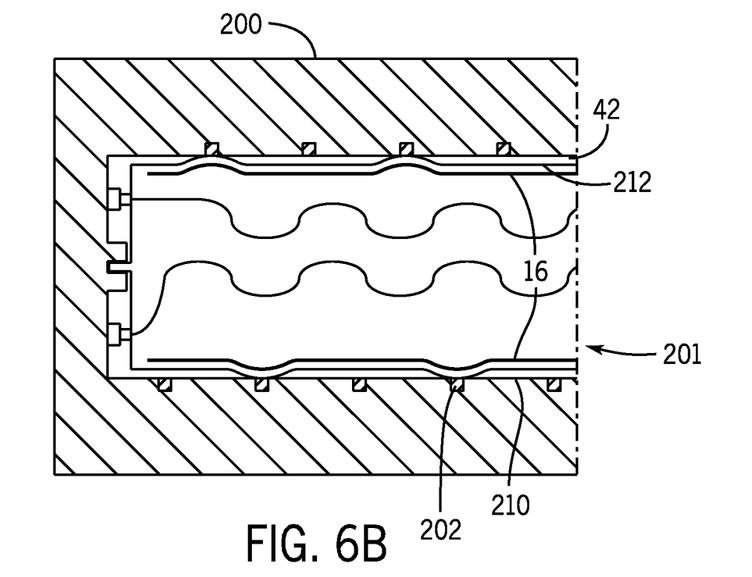
FIG. 6B is a schematic illustration of the magnet-based wire deflector of FIG. 6A in an activated state to deflect a wire of an endoscope.
Figure 6C:
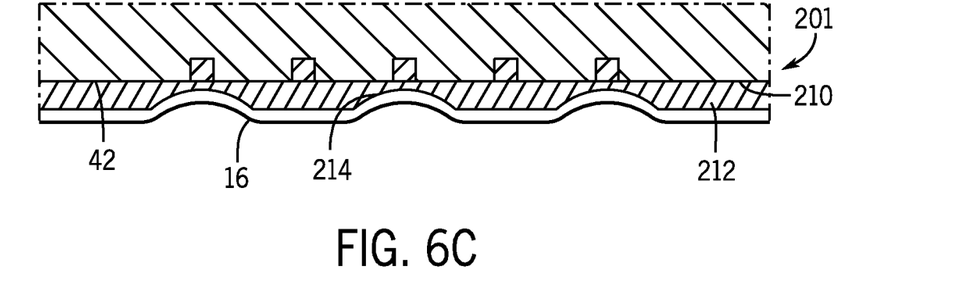
FIG. 6C is a schematic illustration of the magnet-based wire deflector of FIG. 6A in an activated state to deflect a wire of an endoscope.
Figure 7:
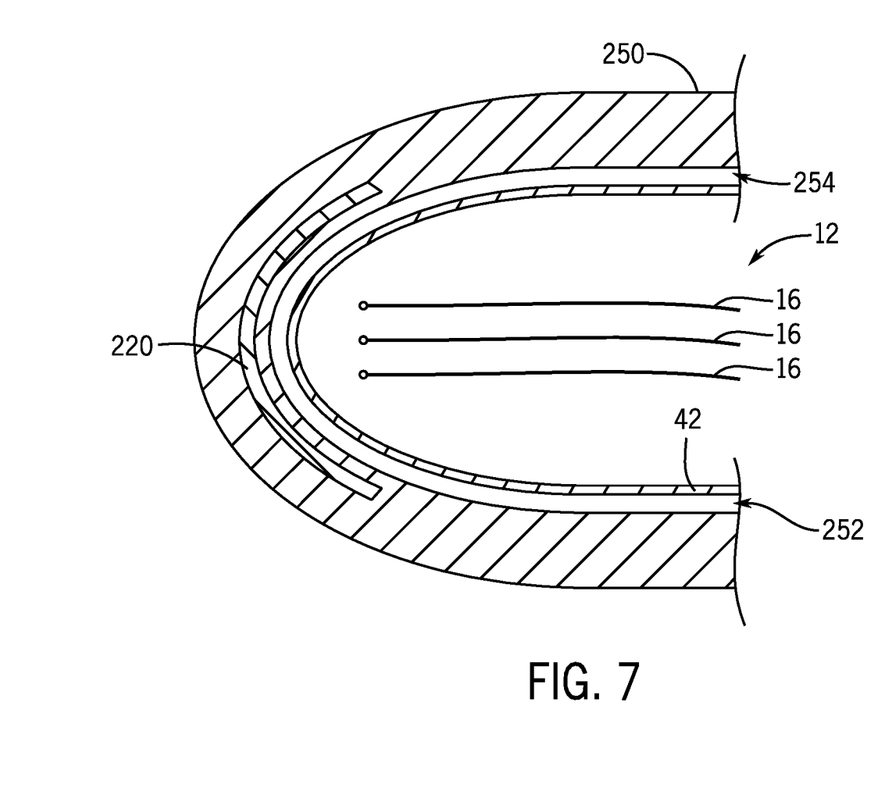
FIG. 7 is a schematic illustration of a connector of a controller device that includes a wire deflector, according to embodiments of the present disclosure.

Portions of a magnet-based wire deflector may be resident in a controller 200 that reversibly couples to the proximal end 24 of the endoscope 12, as shown in FIGS. 6-7. FIGS. 6A-C show the endoscope proximal end 24 inserted into a connector 201 of the controller 200. The connector 201 may be port that is formed within a body of the controller 200. For example, the controller 200 can be a handheld wand or device, and the connector 201 can be configured as a recess or opening formed in the body of the handheld wand. In an embodiment, the controller is a multifunctional visualization instrument that includes an integral display screen, and the connector is formed on or in a rear surface of the display screen.

The connector 201 may be relatively smooth and free of or with limited electrical contacts to facilitate cleaning. Accordingly, in certain embodiments, the connector 201 includes integral wire deflector components that apply force through a smooth and resilient surface of the connector 201 to cause the wire 16 to deflect into conformable or contoured regions of the endoscope 12. Additionally or alternatively, wire deflectors resident on the endoscope 12 may deflect the wire 12 info conformable or contoured regions of the connector 201.

The connector 201 is sized and shaped to accommodate the proximal end 24, e.g., via an interference or threaded fitting. In the illustrated embodiment, the connector 201 includes an array of magnets 202 that, when active, activate the contact surface 210 of the connector 201. In FIG. 6A, the contact surface is not activated, and the wire 16 is in a generally undeflected state. The tubular body 42 is coupled to the contact surface 210, e.g., in direct contact with the contact surface 210.

The wires 16 are arranged towards the tubular body to be close enough to experience the magnetic forces of the magnets 202. The applied deflecting force on the wire 16 is based on the subset of activated magnets 202 in the array. The connector 201 can be shaped in a bore that is sized to fit the endoscope proximal end 24, and the magnets 202 can be located circumferentially around the bore or at particular locations aligned with individual wires 16.

The magnets 202, when activated, attract the wire 16, which is pulled towards the tubular body 12 to create local tension in the wire 16. As shown in FIG. 6B, the contact surface, when activated, can bend the wire 16, causing axial shortening, and also compress or bend an interior wall 212 of the tubular body 42 towards the activated magnets 202. Thus, the endoscope 12 may include compressible or conformable regions that, in response to wire deflection, also change shape to accommodate wire deflection.

In another example, shown in FIG. 6C, the interior surface 212 may include a contoured surface 214, e.g., a resilient contoured surface. Activation of one or more of the magnets 202 draws the wire into the valleys of the contoured surface 214 to cause local tension and axial shortening of the wire.

Turning to FIG. 6A, other electrical connectors, such as leads 220, 224 to a camera, orientation sensor, light source, etc., may be routed in available interior space 43. In contrast to the wires 16, the leads may be relatively slack. The connector 201 may include pins 226, 228 that electrically couple to the camera, orientation sensor, and/or light source. In an embodiment, the rotational orientation of the endoscope 12 is achieved through electrical coupling of endoscope elements to their respective pins 226 228. In an embodiment, the endoscope 12 includes an alignment key 230 that mates with a lock 232 of the connector 201 to align the endoscope 12 in a rotational orientation to position the wires 16 proximate to locations on the connector 201 corresponding to the magnets 202.

FIG. 7 is an arrangement that includes a controller 250 having a curved connector 252. An interior surface 252 of the connector 252 can be activated by activating one or more magnets of a magnet array 256 that is curved to conform to the connector 252. The coupled endoscope 12 may include wires 16 in a side-by-side arrangement that are deflected based on the subset of activated magnets of the magnet array 256.

Figure 8A:
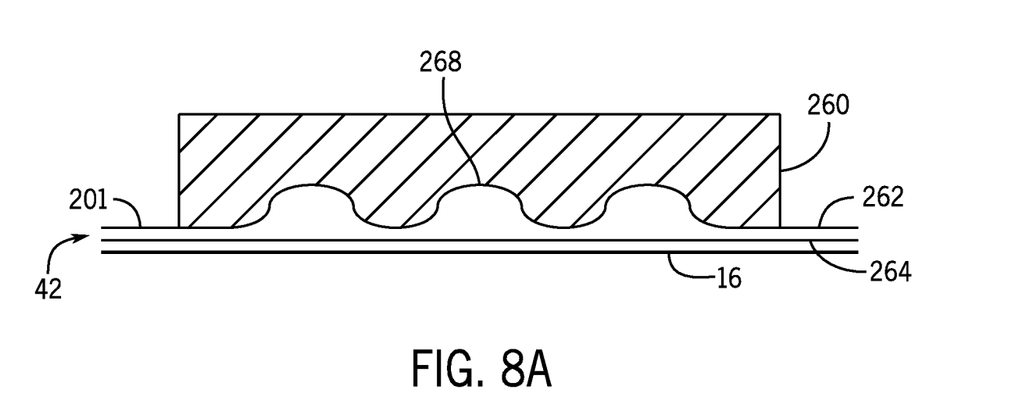
FIG. 8A is a schematic illustration of a connector of a controller device that includes a clamp-based wire deflector, according to embodiments of the present disclosure.
Figure 8B:
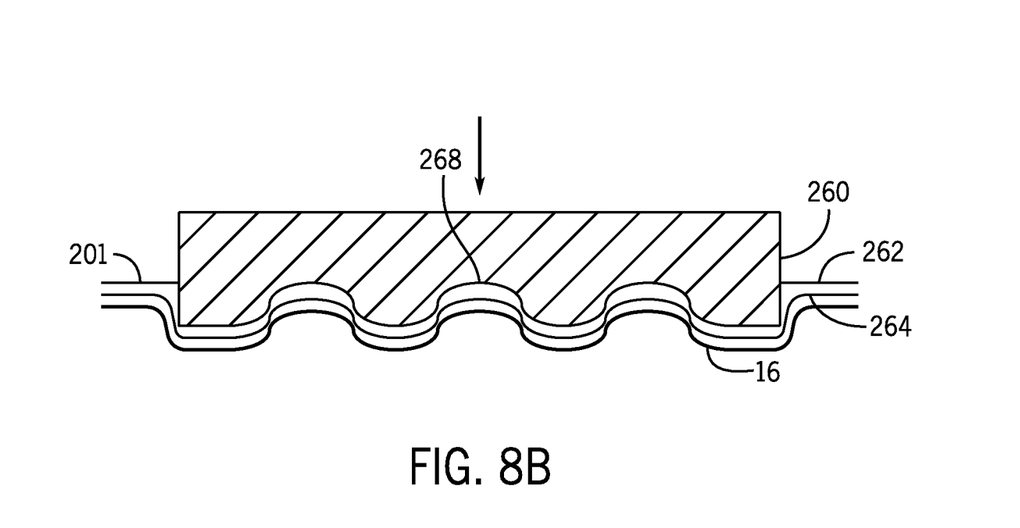
FIG. 8B is a schematic illustration of the clamp-based wire deflector of FIG. 8A in an activated state to deflect a wire of an endoscope.

While certain features of the controller 200 and the connector 201 are illustrated in the context of magnet-based wire deflectors, the connector 201 may additionally or alternatively include one or more clamps. FIG. 8A shows an example of the connector 201 in which a connector clamp 256, in an inactive state, is generally aligned with an interior surface 262 of the connector 201 and applies no or minimal force to a conformable wall 264 of the tubular body 42. When active (e.g., when translated by a motor) as in FIG. 8B, the connector clamp 260 moves towards the conformable wall to cause both the conformable wall 264 and the wire 16 to conformed to a contoured surface of the connector clamp 260.

Figure 9:
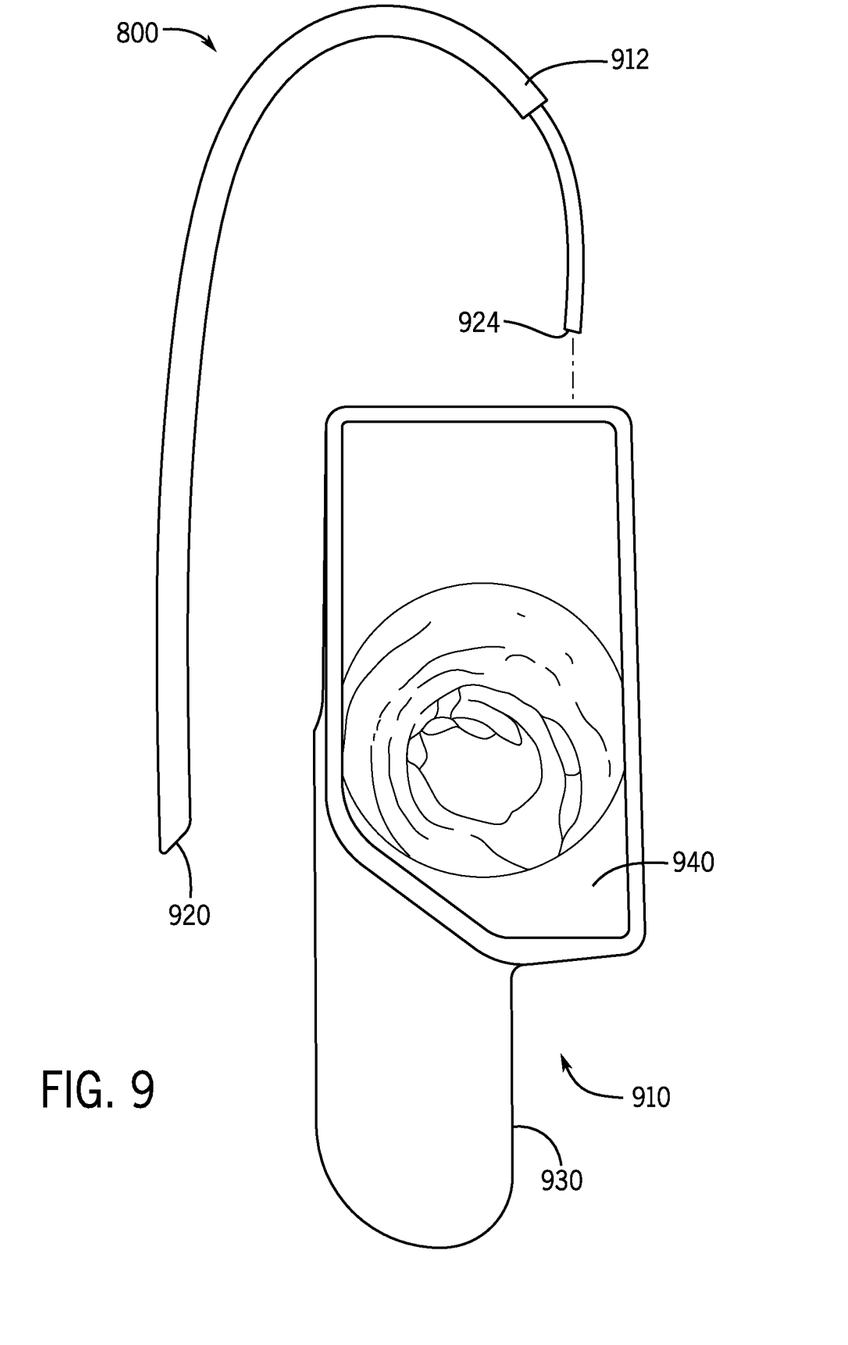
FIG. 9 is a perspective view of a controller and endoscope, according to embodiments of the present disclosure.

The disclosed steerable endoscopes in FIGS. 1-8 may be part of a steerable endoscope system when coupled to a controller that receives steering inputs and that generates instructions to cause wire deflection based on the steering inputs. FIG. 9 is a view of a steerable endoscope system 900. The controller 910 is shown as a hand-held wand 930, and an endoscope 912 is removably connected directly to the wand 930, for passage of control signals from the wand to the endoscope and, when present, video signals from the endoscope 912 to the wand 930. In other embodiments the controller 910 may have other forms or structures. For example, the controller 930 may be a video laryngoscope that couples to a laryngoscope blade, table-top display screen, tablet, laptop, puck, or other form factor.

The controller 910 with the endoscope 912 operates as a two-part endoscope, where the controller 910 serves as the handle, display, and user input to steer a distal end 920 of the endoscope 912. In an embodiment, the controller 910 is reusable and the endoscope 912 is single-use and disposable, to prevent cross-contamination between patients or caregivers.

The proximal end 924 of the endoscope is connected to the controller, and images from a camera at the distal end 920 are displayed on the screen 940. With one hand (such as the left hand), the user taps on the screen 940 to steer the distal end 920, and the endoscope camera, and with the other hand (such as the right hand), the user pushes the endoscope 912 forward into the patient cavity. The endoscope 912 may be passed through an endoscope, in an embodiment, for visualization during intubation.

In an embodiment, the display screen 940 includes a touch screen that is responsive to user steering inputs such as taps, touches, or proximity gestures from the user. For example, the user may enter a touch gesture (such as a tap, double-tap, tap-and-hold, slide, highlight, or swipe) to identify a target point or direction within the image on the screen. This gesture identifies where the user desires to steer the endoscope, and the controller translates this into corresponding instructions for deflecting one or more wires of the endoscope 912 by, in an example, activating magnets, closing a clamp, or applying a non-axial force to a wire. In an embodiment, the steering input may additionally or alternatively be provided via user selection from a menu, selection of soft keys, pressing of buttons, operating of a joy stick, etc.

Figure 10:
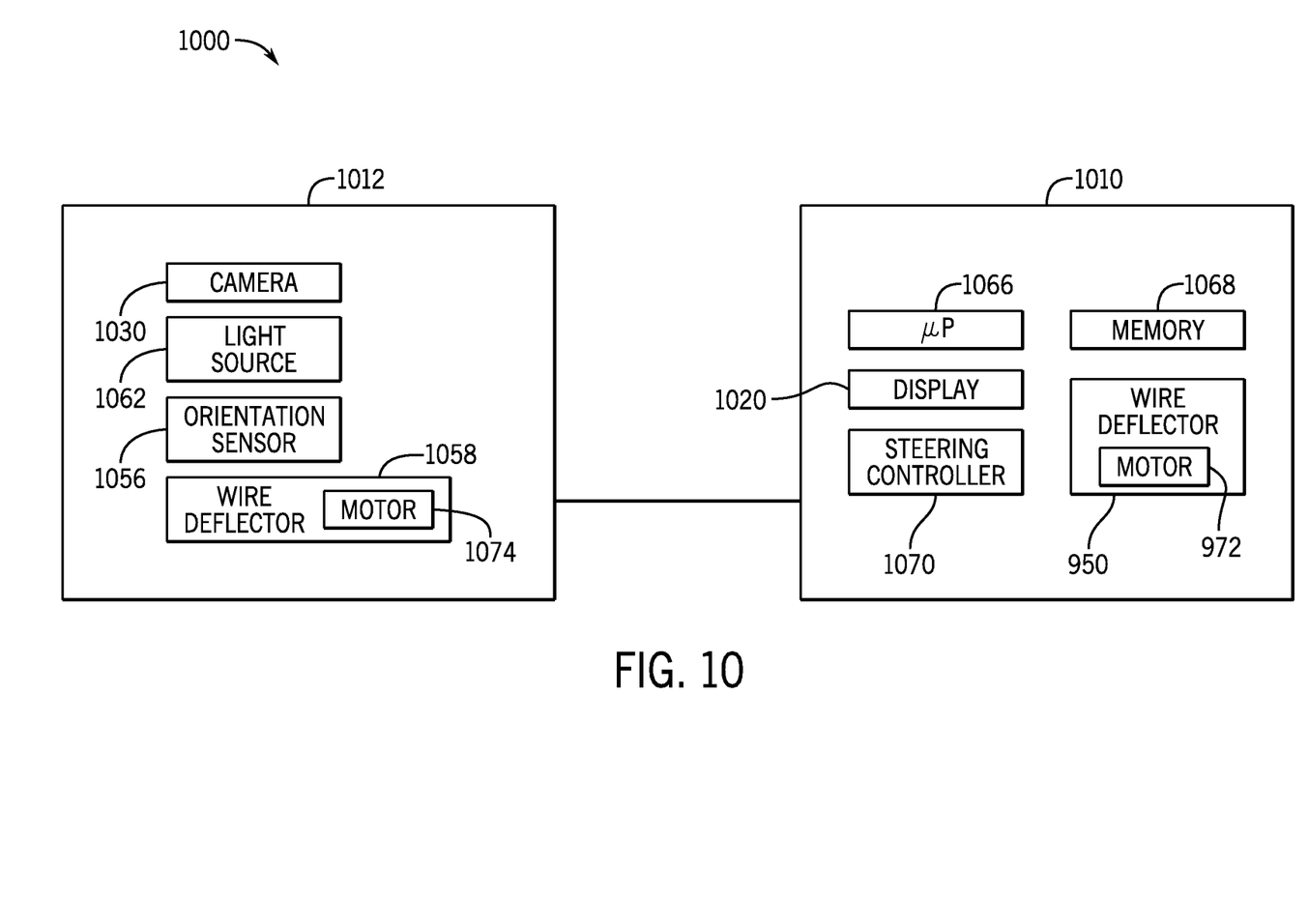
FIG. 10 is a block diagram of a controller and endoscope, according to embodiments of the present disclosure.

A block diagram is shown in FIG. 10, including an endoscope 1012 and a controller 1010. The connection between them may be wired (in which case they each have an electrical connector) or wireless (in which case they each include a wireless transceiver). The endoscope 1012 includes a camera 1030 and, in an embodiment, an orientation sensor 1056 at the distal end of the endoscope 1012. The orientation sensor 1056 may be an inertial measurement unit (INIU), accelerometer, gyroscope, or other suitable sensor. The endoscope 1012 also includes a light source 1062 and a wire deflector 1058 that is coupled to the controller 1010 and receives instructions that cause wire deflection in the endoscope 1012 to change the orientation of the distal end, and camera, of the endoscope 1012.

The orientation sensor 1056 is an electronic component that senses the orientation (such as orientation relative to gravity) and/or movement (acceleration) of the distal end of the endoscope and provides a signal indicating a change in the endoscope's orientation and/or a motion of the endoscope 1012 in response to steering.

The controller 1010 includes a processor 1066 or chip (such as a chip, a processing chip, a processing board, a chipset, a microprocessor, or similar devices), a hardware memory 1068, a display screen 1020 (such as a touch screen), and a wire deflector controller 1070, which may include a controller to activate any wire deflector components, such as magnets, that are resident on the controller. The controller 1010 includes a display 1080 and may also include some other type of user input (buttons, switches), and a power source (such as an on-board removable and/or rechargeable battery).

The controller 1010 may also include a power source (e.g., an integral or removable battery) that provides power to one or more components of the endoscope as well as communications circuitry to facilitate wired or wireless communication with other devices. In one embodiment, the communications circuitry may include a transceiver that facilitates handshake communications with remote medical devices or full-screen monitors. The communications circuitry may provide the received images to additional monitors in real time.

The processor 1066 may include one or more application specific integrated circuits (ASICs), one or more general purpose processors, one or more controllers, FPGA, GPU, TPU, one or more programmable circuits, or any combination thereof. For example, the processor may also include or refer to control circuitry for the display screen 1080. The memory may include volatile memory, such as random access memory (RAM), and/or non-volatile memory, such as read-only memory (ROM). The memory may include stored instructions, code, logic, and/or algorithms that may be read and executed by the processor to perform the techniques disclosed herein and drive the wire deflector controller 1070.

The wire deflector 1058 of the endoscope 1012 and/or the wire deflector 1050 controller 1010 may include the wire deflectors (clamps, magnets) as provided in the disclosed embodiments and associated drivers of movable wire deflector components, such as actuators or servo motors (e.g., motor 1072 of the wire deflector 1050 and/or motor 1074 of the wire deflector 1058). In an embodiment, the motor drives back and forth type translation motions (e.g., not spinning motions) to drive movement of a clamp or other wire deflection components. Accordingly, a relatively fast and efficient motor (e.g., operating at 200 Hz or greater) for linear motion control may be used to drive such motion. In an embodiment, the motor drives pinching or spooling/coiling of the wire 16.

Figure 11:
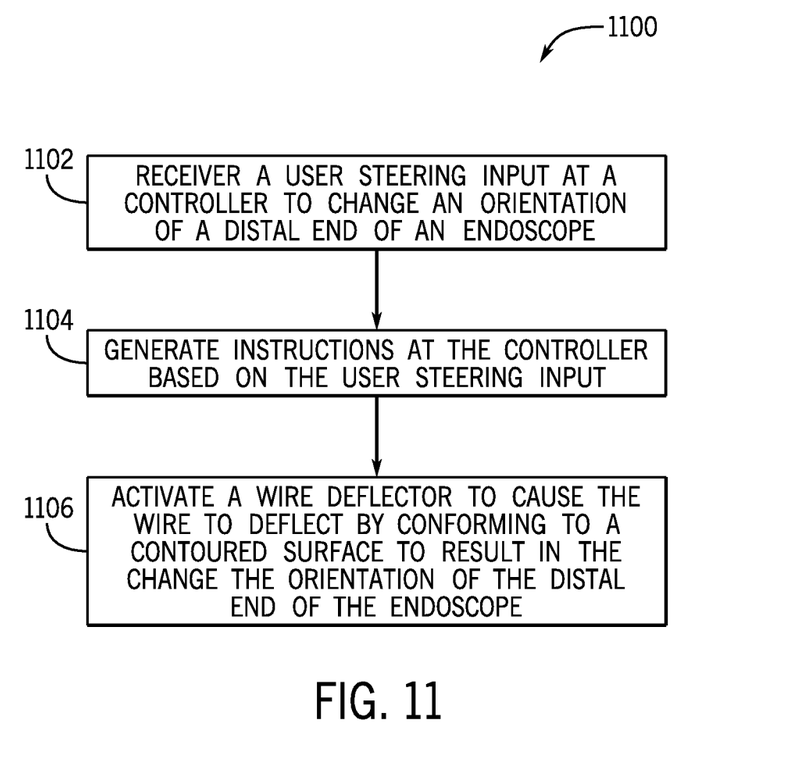
FIG. 11 is a flowchart depicting a method for steering of an endoscope via a wire deflector, according to embodiments of the present disclosure.

FIG. 11 is a process flow diagram of a computer-controlled method 1100 of steering an steerable endoscope and with reference to features discussed in FIGS. 1-10, in accordance with an embodiment of the present disclosure. The method 1100 disclosed herein includes various steps represented by blocks. It should be noted that at least some steps of the method 1100 may be performed as an automated procedure by a system, such as the system 1000. Although the flow chart illustrates the steps in a certain sequence, it should be understood that the steps may be performed in any suitable order and certain steps may be carried out simultaneously, where appropriate. Additionally, steps may be added to or omitted from of the method 1100. Further, certain steps or portions of the method 1100 may be performed by separate devices. For example, a portion of a method 1100 may be performed by the controller, while other portions of the method 1100 may be performed by the endoscope.

The method 1100 initiates with the step of receiving a user steering input at a controller to change an orientation of a distal end of the endoscope (block 1102). The controller receives the user steering input and, based on the user steering input, generates instructions at the controller (block 1104). Such instructions may include activation of one or more wire deflectors, and may include activating a magnet, activating a clamp to clamp a wire, and/or deploying a retractable pin or paddle. The location of the activated element may be selected based on the steering input. For example, steering in particular x-y-z directions may involve coordinated deflection of two or more wires of the endoscopes in a particular direction and with a particular force. The generated instructions are used to activate the appropriate wire deflectors to deflect one or more wires to cause a change in the orientation of the endoscope distal end (block 1106) by causing the one or more wires to conform to a contoured surface. The contoured surface may be an integral or interior surface of the endoscope, a clamp surface, and/or a surface of a port of a controller. The wire deflector can cause the wire to conform to the contoured surface by directly contacting the wire and applying a mechanical force to bend the wire around contours of the contoured surface. The wire deflector, when active, can activate a magnet or set of magnets that attract the wire (e.g., a metal wire) towards the magnets and, in turn, towards the contoured surfaces that include the magnets. Changing the orientation of the distal end causes a camera at the distal end to change orientation. Thus, the user can change the camera view via endoscope steering as provided herein and navigate within the patient airway by combinations of changing orientation at the distal end and forward/backward movement of the endoscope by the user.

In an embodiment, the controller may receive feedback from an orientation sensor of the endoscope that is also used to generate the instructions. The rotational or absolute sensor orientation may be used by the controller to determine which wire or wires, distributed circumferentially about the distal end, should be deflected to steer the endoscope in the direction indicated by the user steering input.

The disclosed techniques are discussed in the context of steering an endoscope, such as those used for endotracheal intubation. It should be understood that the disclosed techniques may also be useful for steering devices used in other types of airway management or clinical procedures. For example, the disclosed techniques may be used in conjunction with placement of other devices within the airway, secretion removal from an airway, arthroscopic surgery, bronchial visualization past the vocal cords (bronchoscopy), tube exchange, lung biopsy, nasal or nasotracheal intubation, etc. In certain embodiments, the disclosed devices may be used for steering and navigation within the anatomy (such as the pharynx, larynx, trachea, bronchial tubes, stomach, esophagus, upper and lower airway, ear-nose-throat, vocal cords). The disclosed devices may also be used for or in conjunction with suctioning, drug delivery, ablation, or other treatments of tissue and may also be used in conjunction with endoscopes, bougies, blind introducers, scopes, or probes.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A steerable endoscope system, comprising:
an endoscope comprising:
  a tubular body;
  a plurality of wires disposed within the tubular body, wherein each wire of the plurality of wires is coupled to an endoscope distal end such that, upon deflection of one or more wires of the plurality of wires in a non-axial direction, the endoscope distal end changes orientation;
a controller in communication with the endoscope and comprising:
  a display screen responsive to a user command to steer the endoscope; and
  a processor that receives the user command and generates instructions to change the orientation of the endoscope distal end; and
at least one clamp having clamp sections, wherein the instructions cause the clamp sections to move closer together such that at least one of the one or more wires follows a contoured surface of one or more of the clamp sections, under a clamping force of the at least one clamp, to cause the change to the orientation of the endoscope distal end.

2. The steerable endoscope system of claim 1, wherein the at least one clamp, when activated, moves in a non-axial direction relative to the one or more wires to clamp the one or more wires.

3. The steerable endoscope system of claim 1, wherein the endoscope further comprises a camera at the endoscope distal end.

4. The steerable endoscope system of claim 1, wherein each wire of the plurality of wires is coupled to a distal support and to a proximal support such that each wire is taut with substantially no load when the clamp is not activated.

5. The steerable endoscope system of claim 1, wherein the endoscope further comprises a spacer disposed within a central passage of the tubular body, wherein the plurality of wires extend through the spacer with first spacing relative to one another and are coupled to the endoscope distal end with a second spacing relative to one another, wherein the first spacing is smaller than the second spacing.

6. The steerable endoscope system of claim 5, wherein the second spacing comprises a circumferential spacing about a circumference of the tubular body and wherein the first spacing comprises a side-by-side arrangement within the tubular body.

7. The steerable endoscope system of claim 5, wherein the spacer is disposed closer to the endoscope distal end than an endoscope proximal end.

8. The steerable endoscope system of claim 1, wherein an interior surface of the endoscope is contoured such that the one or more wires conform to the interior surface when clamped by the at least one clamp.

9. The steerable endoscope system of claim 1, wherein the at least one clamp is disposed within the controller and, when activated, clamps around a proximal end of the one or more wires that extends from the endoscope.

10. The steerable endoscope system of claim 1, wherein the contoured surface is sinusoidal.

11. The steerable endoscope system of claim 1, wherein the endoscope is removable from the controller and disposable, and wherein the controller is reusable.

12. The steerable endoscope system of claim 1, wherein the clamp sections are part of a first clamp that clamps a first wire of the one or more wires, and the steerable endoscope system further comprises a second clamp that clamps a second wire of the one or more wires.

13. An endoscope system, comprising:
an endoscope comprising:
a tubular body comprising a plurality of wires, wherein each wire of the plurality of wires is coupled to an endoscope distal end and an endoscope proximal end and wherein the endoscope distal end is at a first orientation when the plurality of wires are not deflected; and
a controller in communication with the endoscope that receives a user steering input and that generates instructions to cause clamping of a clamp, between one or more clamp sections having contoured surfaces, such that the one or more clamp sections move closer together to cause at least one wire of the plurality of wires to follow the contoured surface under a clamping force of the clamp, which causes deflection of the endoscope distal end to a second orientation that is different than the first orientation.

14. The endoscope system of claim 13, wherein the clamp sections are disposed within the controller.

15. The endoscope system of claim 13, wherein the instructions to cause coordinated deflection further activate a plurality of magnets that magnetically attract one or more of the plurality of wires.

16. The endoscope system of claim 13, wherein the plurality of wires comprises at least three wires, and wherein the instructions to cause coordinated deflection cause simultaneous deflection of the at least three wires.

17. An endoscope, comprising:
a tubular body comprising a proximal end and a distal end;
a plurality of wires within a central passage of the tubular body and extending from the distal end towards the proximal end; and
a clamp that, when activated, causes clamp sections of the clamp to move closer together such that at least one of the wires of the plurality of wires follows contoured surfaces of the clamp sections, under a clamping force of the clamp, to cause a change in orientation of the distal end.

18. The endoscope of claim 17, wherein at least one of the clamping sections has a sinusoidal contoured surface.

19. The endoscope of claim 17, wherein each clamping section has a sinusoidal contoured surface.

20. The endoscope of claim 17, wherein the clamp is a first clamp that clamps a first wire of the plurality of wires, and the endoscope further comprises a second clamp that clamps a second wire of the plurality of wires.

\* \* \* \* \*